United States Patent [19]

Dugot

[11] Patent Number: 4,667,683

[45] Date of Patent: May 26, 1987

[54] AUDIOMETER

[75] Inventor: Richard S. Dugot, New York, N.Y.

[73] Assignee: Biolectron, Inc., Hackensack, N.J.

[21] Appl. No.: 743,509

[22] Filed: Jun. 11, 1985

[51] Int. Cl.[4] .............................................. A61B 5/12
[52] U.S. Cl. .................................... 128/746; 73/585; 128/420.5
[58] Field of Search ........................ 128/746, 731–733, 128/421–422; 179/1.5 FS, 107 R; 73/585

[56] References Cited

U.S. PATENT DOCUMENTS

| | | | |
|---|---|---|---|
| 3,563,246 | 2/1971 | Puharich et al. | 128/422 |
| 3,586,791 | 6/1971 | Puharich et al. | 128/1 R X |
| 4,284,847 | 8/1981 | Besserman | 128/746 X |
| 4,462,411 | 7/1984 | Richards | 128/746 |
| 4,489,610 | 12/1984 | Slavin | 128/746 X |
| 4,515,169 | 5/1985 | Ward | 128/746 |
| 4,556,069 | 12/1985 | Dalton, Jr. et al. | 128/746 |

Primary Examiner—Kyle L. Howell
Assistant Examiner—Angela D. Sykes

[57] ABSTRACT

Audiometer apparatus comprises an electrostatic transducer having insulated electrodes for application to the skin on the head of a patient and driven by an ultrasonic frequency carrier signal generated in a series resonant circuit including the impedance of the body tissues between the electrodes, the carrier frequency being determined by the series resonant circuit. The amplitude of the carrier is modulated at an audio frequency, and operating parameters such as the magnitude of the current fed to the electrodes and the modulation frequency are controlled automatically in response to preselected values preset therein.

Current and modulation frequency values are preset stepwise into a manually adjustable preselectors having detents formed by cooperating magnetic elements establishing successive rest positions corresponding to steps to which the preselector may be set. The preselector is formed with spaced apart segments disposed to cooperate with a pair of optointerruptors to cause the latter to generate stepping pulses and pulses indicating the direction of adjustment of the preselector.

6 Claims, 5 Drawing Figures

AUDIOMETER

BACKGROUND OF THE INVENTION

This invention relates to apparatus for auditory diagnosis and, more particularly, to new and improved audiometer apparatus utilizing electrical stimulation which is capable of providing very accurate diagnostic information about the hearing of a patient in a simple and highly effective manner.

It has long been known that the sensation of hearing can be created by stimulating a patient electrically by an audio modulated carrier signal of ultrasonic frequency applied through electrodes in contact with the skin in the region of the facial nerve system. The prior U.S. Pat. Nos. 3,563,246 and 3,586,791 disclose systems of this general character for stimulating hearing in hearing-deficient persons, in which LC series resonant coupling at carrier frequency is maintained between a signal source and the human subject so as to minimize the effect of changes in the impedance of the latter on the resonant frequency and to maximize the transfer of effective auditory information to the subject.

It is an object of the invention to provide new and improved audiometer apparatus, based on the electrical stimulation principles taught in the foregoing patents, which is capable of improved control of biotransduced energy, stability and precision.

SUMMARY OF THE INVENTION

Audiometer apparatus according to the invention utilizes an electrostatic transducer comprising a pair of insulated metal electrodes applied to the skin of a patient, one on the mastoid or tragus and the other on the other mastoid or tragus or on an arm, for example, and driven by an ultrasonic frequency carrier signal generated in a series resonant circuit including the impedance of the body tissues between the electrodes, the frequency of the voltage generator being determined by the series resonant circuit. The amplitude of the carrier signal is modulated successively by audio signals of different frequencies and operating parameters such as the magnitude of the current supplied to the electrodes and the modulation frequency are precisely controlled automatically by a microprocessor in response to preselected values set therein by the audiologist conducting a test of the auditory sensitivity of a patient.

The striking result achieved with audiometric apparatus according to the invention is the perception by the listener being tested of high fidelity pure tones and voice and broad spectrum signals, ranging up to 20 KHz, without involvement of traditional acoustic transducers or the influence of the outer and middle ear structures.

Current magnitude selection is accomplished by comparing the measured output current to a selected value preset in the microprocessor and utilizing the output of the comparison to adjust a digital attenuator controlling the output current until the two values are equal.

Selection of the modulation audio frequency is effected by generating a digital number corresponding to a specific preselected frequency and adjusting a voltage controlled oscillator in response thereto to supply a signal of the preselected frequency to means for effecting amplitude modulation of the carrier signal supplied to the electrodes.

The invention also contemplates the provision of novel, manually settable, quiet magnetic detent means for generating digital information accurately representative of selected current and audio frequency values for use in controlling the microprocessor to maintain the selected output current amplitude and modulating audio frequency values constant.

DESCRIPTION OF A PREFERRED EMBODIMENT

The invention may be better understood from the following detailed description, taken in conjunction with the accompanying drawings in which.

Figure 1:
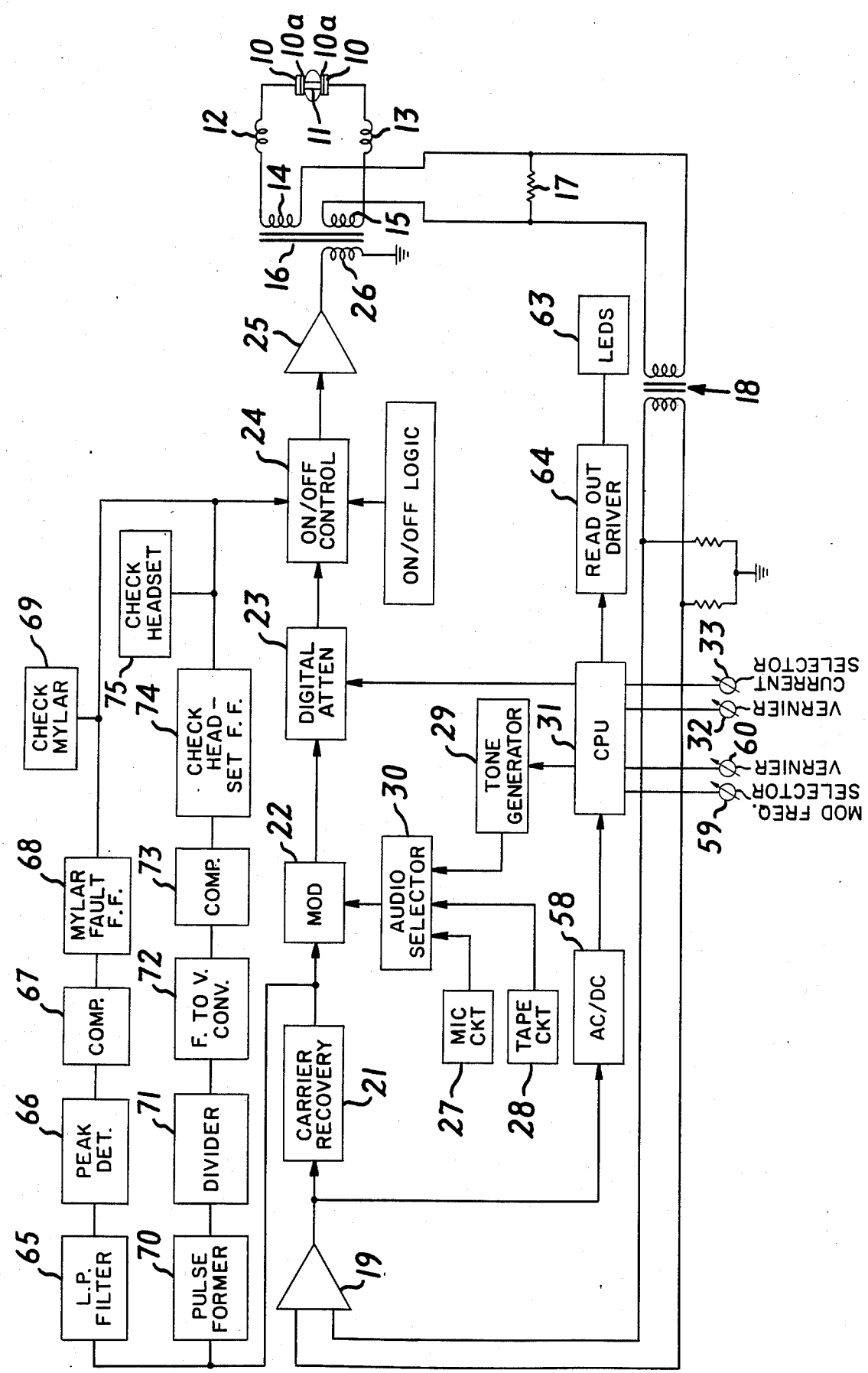
FIG. 1 is a schematic diagram of audiometer apparatus constructed according to the invention.

Audiometer apparatus according to the invention utilizes the capacitive coupling principle disclosed in the prior art U.S. Pat. No. 3,586,791 to apply a high frequency carrier signal, amplitude modulated at an audio frequency, to the skin on opposite sides of the patient's head by means of a pair of metal electrodes 10 mounted on a headband 11 and insulated from the skin by Mylar covers 10a, for example. The electrodes 10 are connected in a series resonant circuit including two fixed, high Q inductors 12 and 13, the output windings 14 and 15 of an output transformer 16, and a resistor 17. Since the capacitance of the Mylar-skin interface is one of the elements of the circuit, and is variable, the series resonant circuit comprising the Mylar-skin interface and the fixed inductors 12 and 13 is used to determine the frequency of the carrier signal applied to the head of the patient. The carrier frequency should lie in the range 40–100 KHz, e.g. 60 KHz.

To this end, the voltage across the resistor 17, which is a measure of the current in the resonant circuit, is fed back positively through a feedback transformer 18 to an input amplifier 19. The amplifier 19 is part of a signal generator including a carrier recovery stage 21, an audio amplitude modulator 22, a digital attenuator 23, an On-Off control 24, and a power amplifier 25, the output of which is fed to the primary winding 26 of the transformer 16. Since the overall feedback is positive, the circuit will maintain oscillation at the frequency determined by the inductors 12 and 13 and the Mylar-skin capacity at the Mylar-covered electrodes 10.

The modulator 22 is connected to receive modulating signals selectively from a microphone 27, a magnetic tape player 28, or an audio tone generator 29 described in greater detail below, selection being effected by a manual audio selector 30 which supplies the selected modulating signal to the modulator 22. The carrier recovery and amplitude control circuit 21 serves to strip the modulation off the carrier in the known manner so that the signal entering the modulator 22 consists only of a constant amplitude carrier voltage, which becomes modulated anew each time around. Since the modulating signal is controlled with great precision in the audio tone generator 29, and the amplitude of the carrier supplied from the carrier recovery circuit is constant, the signal at the input to the digital attenuator 23 is constant.

In a typical instrument, the output current supplied to the electrodes 10 may be adjustable over a range of, say, 0.25 ma to 30 ma in 0.25 ma steps. Current magnitude selection is accomplished by generating a digital representation of the output current desired, and entering the digital representation into a microprocessor (CPU) 31 where it is compared with a digital representation of the output current to provide a control signal to the digital attenuator to adjust the output current to the desired preset value.

Generation of a digital representation of a desired output is accomplished by presetting manually operable current selectors 32 and 33 (FIGS. 1 and 3A, 3B and 3C), the former enabling adjustment of the current in small steps of, say, 0.25 ma and the latter enabling adjustment in larger steps up to a maximum of, say, 30 ma. Adjustment is effected by manipulation of one or both of the dials 34 and 35 on a housing 36 (FIG. 2), which also contains the components of the current selectors 32 and 33 and the circuitry shown in FIG. 1. Since the current selectors are substantially identical, it will be necessary to describe only one in detail.

Figure 3A:
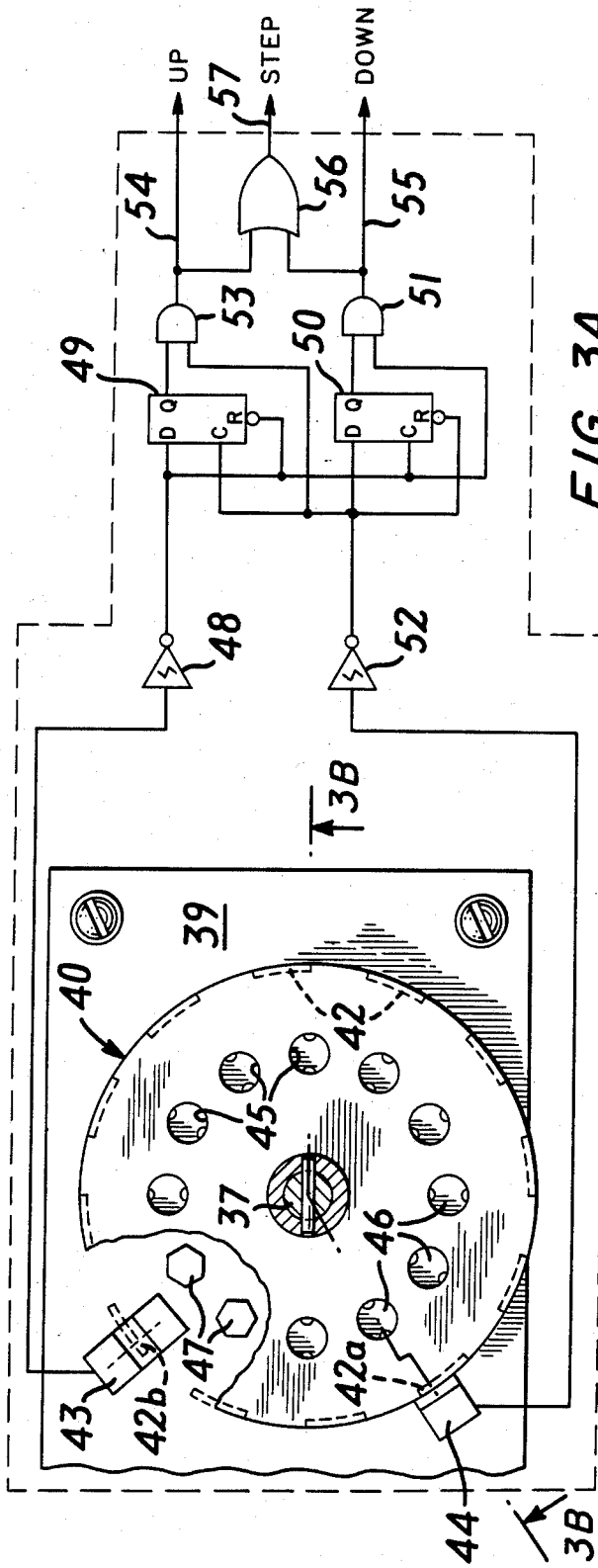
FIG. 3A is a top view, partly in section, taken along the line 3A—3A of FIG. 3B, looking in the direction of the arrows, of manually adjustable selector means and circuitry therefor that may be employed for presetting current or audio frequency values in the audiometer apparatus shown in FIG. 1.
Figure 3C:
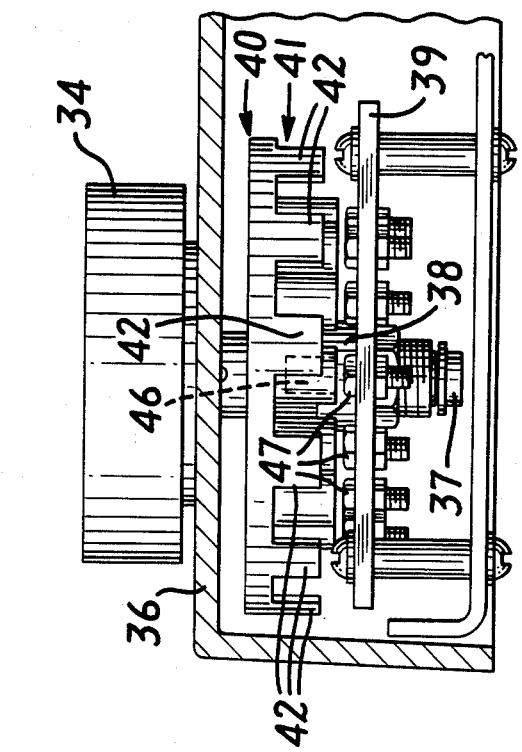
FIG. 3C is a side view of the selector shown in FIGS. 3A and 3B.
Figure 3B:
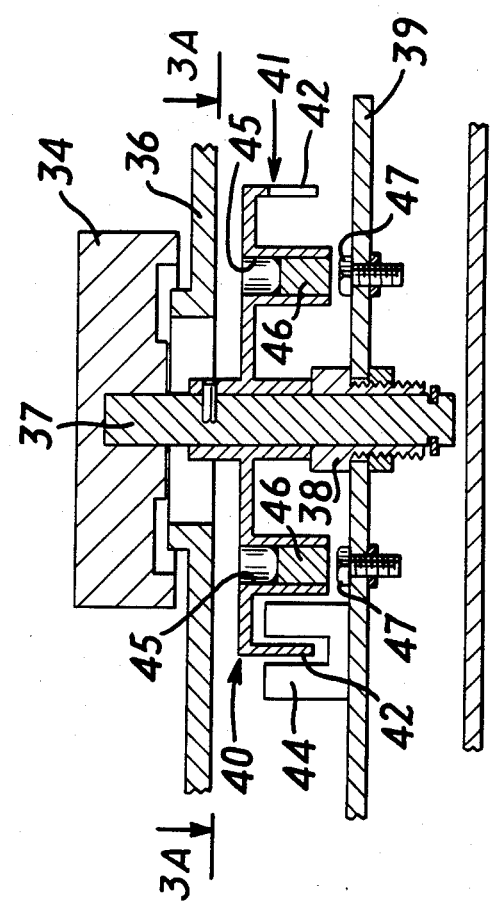
FIG. 3B is a view, in section, taken along the line 3B—3B of FIG. 3A, looking in the direction of the arrows.

As best shown in FIGS. 3A, 3B and 3C, the dial 34 for the current selector 32 is mounted on a shaft 37 rotatable in a hub 38 supported on a printed circuit board 39 in the housing 36. Also mounted on the shaft 37 for rotation therewith is a rotor 40 having a downwardly depending skirt 41 at the outer periphery thereof. The skirt 41 is formed with a plurality (twelve in the typical embodiment shown) of equally spaced arcuate segments 42 (FIG. 3B) which are adapted to be swept past a pair of optointerruptors 43 and 44. The latter are positioned asymmetrically so that, at any setting of the dial 34, both are interrupted, one by an end portion 42a of a segment 42 and the other by an opposite end portion 42b of another segment 42, respectively, so that they respond successively when the dial 34 is rotated in either direction, the order of response depending on the direction of rotation.

Formed in the rotor 40 is a circular array of equally angularly spaced apart bores 45, in each of which is seated a permanent magnet 46. Affixed to the printed circuit board 39 substantially in registry with the permanent magnets 46 are a plurality of flat screw heads 47 made of magnetic material. When the dial 34 is rotated, the magnetic fields between the magnets 46 and the screw heads 47 are alternately broken and reestablished, providing a very distinct tactile detent feel to the person turning the dial.

The outputs from the optointerruptors 43 and 44 are normally high. When the dial 34 is turned clockwise, the optointerruptor 43 opens before the optointerruptor 44 so that the former goes low before the latter. When the dial 34 is turned counterclockwise, however, the optointerruptor 44 goes low before the optointerruptor 43. The output of the optointerruptor 43 is fed through an inverter 48 (FIG. 3A) to the D and R pins of a flip-flop 49, to the pin C of a flip-flop 50 and one terminal of an AND gate 51, the other terminal of which is connected to the Q pin of the flip-flop 50.

The output of the optointerruptor 44, similarly, is fed through an inverter 52 to the D and R pins of the flip-flop 50, to the C pin of the flip-flop 49, and to one terminal of an AND gate 53, the other terminal of which is connected to the Q pin of the flip-flop 49. The AND gates 53 and 51, respectively, supply UP and DOWN signals to the CPU 31 over the conductors 54 and 55, respectively, and provide inputs to an OR gate 56 which supplies step pulses to the CPU 31 over the conductor 57 as described below.

In operation, when the dial 34 is turned clockwise so that the optointerruptor 43 goes low first, the D and R pins of the flip-flop 49 and the C pin of the flip-flop 50 go high. When the optointerruptor 44 goes low shortly thereafter as the dial 34 is moved one step, the pin C of the flip-flop 49 and one input to the AND gate 53 both go high. Since the high signal on the C pin of the flip-flop 49 sets the Q pin thereof high, the outputs of both the AND gate 53 and the OR gate 56 go high, providing an UP pulse on the conductor 54 and a STEP pulse on the conductor 57.

For the reverse rotation of the dial 34, the optointerruptor 44 goes low before the optointerruptor 43, but this time the outputs of both the AND gate 51 and the OR gate 56 go high. This supplies a DOWN pulse over the conductor 55 and a STEP pulse on the conductor 57.

The current selector 33 is similar to the current selector 32 and it provides UP, DOWN and STEP signals to the CPU 31 as its dial 35 is turned clockwise or counterclockwise to adjust the current value upwardly or downwardly.

In operation, the computer 31 (FIG. 1) generates from the pulses supplied to it by the selectors 32 and 33 a digital representation of the current value preselected by manipulation of the dials 34 and 35 and stores it in a random access memory. The measured current from the amplifier 19 is converted to a DC voltage by a precision AC to DC converter 58 which is calibrated to deliver a voltage exactly proportional to the output current, and the latter voltage is fed to an analog to digital (A/D) converter in the CPU 31, the digital output of which is continuously compared to the digital representation of the preset current value. If they differ, corrective digital information is fed into a latch in the CPU 31 and then transmitted to the digital attenuator 23 to cause the latter to adjust the current to the electrodes 10 precisely to the preset value. The CPU 31 continuously interrogates the settings of the selectors 32 and 33 and acts to adjust the attenuator 23 to correct the gain in the resonant loop as required to maintain the current accurately at the preset value.

Figure 2:
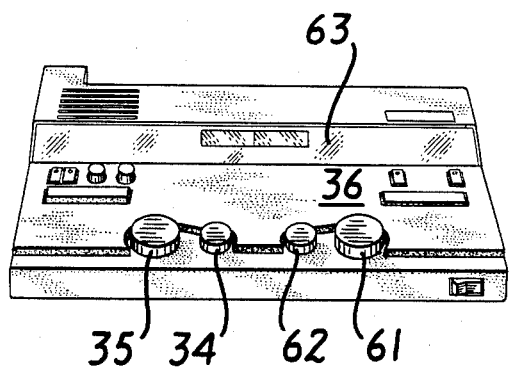
FIG. 2 is a front view of a typical housing and control panel for the apparatus shown in FIG. 1.

The modulating audio frequency is selected by audio selectors 59 and 60 actuated by dials 61 and 62, respectively, mounted on the housing 36, as shown in FIG. 2. The audio selectors 59 and 60 may provide frequency selection from 100 Hz to 20,000 Hz, the former providing coarse adjustment in 1 KHz steps and the latter fine adjustment in 100 Hz steps. They are similar in construction and operation to the current selectors 32 and 33 and each of them provides UP and DOWN and STEP pulses to the CPU 31 which generates therefrom a digital representation of the preselected frequency. A digital-to-analog converter in the CPU 31 converts the digital representation of the preset frequency to an analog value, which is fed to a voltage controlled sine wave oscillator in the tone generator 29, causing the latter to generate an audio signal precisely at the preset frequency value. That audio signal is fed to the modulator 22 to modulate the ultrasonic frequency carrier at the preselected audio frequency.

The audio frequency and current magnitude may be displayed by light-emitting diodes (LED) on a display panel 63 on the housing 36. The diodes may be controlled by a conventional eight digit LED driver system 64 responsive to the CPU 31.

When the Mylar film covering the electrodes is punctured, the capacity of the Mylar-skin interface increases and the carrier frequency decreases proportionally. In order to detect such a condition, the output from the carrier recovery stage 21 is fed through a low pass filter 65 and a peak detector 66 to a comparator 67. The decreased carrier frequency caused by such a condition is detected by the low pass filter, setting a flip-flop 68 and actuating an ON-OFF flip-flop in the ON-OFF control 24 to shut off the equipment. At the same time, a CHECK MYLAR indicator 69 on the housing 36 is lit, warning the operator of the existence of the condition.

Also, when the headset on which the electrodes 10 are mounted is not properly set on the patient's skin, the Mylar-skin interface capacity decreases and the carrier frequency increases proportionally. This condition is detected by passing the output from the carrier recovery stage 21 through a channel including a pulse former 70, a divider 71, and a frequency-to-voltage converter 72, the output of which is fed to a comparator 73 and associated flip-flop 74. Upon occurrence of the improper headset condition, the voltage output from the frequency-to-voltage converter 72 increases and activates the comparator 73, setting the flip-flop 74, which in turn shuts off the instrument by actuating a signal ON-OFF flip-flop in the ON-OFF control 24. At the same time, a CHECK HEADSET indicator 75 on the housing 36 is activated, warning the operator.

In testing the auditory sensitivity of a patient, one of the Mylar-covered electrodes 10 may be placed on one mastoid or tragus of the patient and the other on the other mastoid or tragus or on another part of the body such as an arm, for example. Then the auditory thresholds at different frequencies for the patient may be determined by adjustment of the modulation frequency selectors 59 and 60 and the current selectors 32 and 33 in the customary manner.

The invention thus provides a highly effective non-acoustic audiometer which utilizes electrical stimuli to assess the level of otologic deficiency present in a patient. The controls are simple and easy to use, yet they allow precise and reliable adjustments of the stimulating current and of the audio frequency to be made stepwise up to a frequency of 20 KHz. For the first time, the invention makes high frequency diagnostic testing possible as required in the direct cochlear assessment of high frequency sensitivity.

It will be understood that apparatus according to the invention is not limited to the testing of hearing as described above. It can be used effectively in any application in which it is desired to apply to a living body amplitude modulated carrier signals of ultrasonic frequency and accurately preset magnitude and audio modulating frequency, as in the method disclosed in the co-pending U.S. application Ser. No. 722,997 filed Apr. 15, 1985, by Joseph L. Lawrence, for "Methods for Applying Electrical Stimulation Signals to Damaged Bone and Soft Tissue for Promoting Healing", for example.

The specific embodiment described above is intended only to be illustrative, and modifications in form and detail are possible within the scope of the following claims.

I claim:

1. An automatic apparatus comprising
   a series resonant circuit having electrode terminals for application to the skin of a living body so as to include the body impedance in said circuit,
   oscillator means including said series resonant circuit for supplying to the latter a carrier signal at a high frequency determined by said resonant circuit,
   means for modulating the amplitude of said carrier frequency at an audio frequency,
   audio signal generator means controllable to supply modulating signals at different audio frequencies to said modulating means,
   attenuator means selectively controllable to adjust the amplitude of the amplitude of the carrier signal supplied to said series resonant circuit to a selected value, in which the improvement comprises
   means responsive to the amplitude of the carrier signal supplied to said series resonant circuit for generating a first digital representation thereof,
   first adjustable means for generating a second digital representation of a selected value of said carrier signal amplitude, and
   means jointly responsive to said first and second digital representations for controlling said attenuator means to maintain the amplitude of the carrier signal supplied to said resonant circuit at said selected value.

2. Apparatus as in claim 1 with
   second means adjustable to generate a third digital representation of a selected audio modulating frequency, and
   means responsive to said third digital representation for controlling said audio signal generator means to generate an audio modulating signal at said selected frequency.

3. Apparatus as in claim 2 in which said second adjustable means comprises
   means adjustable stepwise in opposite directions to select a predetermined audio modulating frequency for supply to said amplitude modulating means and
   means responsive to stepwise adjustment of said last named means for generating stepping pulses and pulses indicative of the direction of adjustment thereof.

4. Apparatus as in claim 2 in which said means responsive to said third digital representation comprises digital to analog converter means for converting said digital representation to an analog value, and said audio signal generator means comprises voltage controlled oscillator means responsive to said analog value for generating an audio modulating voltage at a selected frequency.

5. Apparatus as in claim 1 in which said first adjustable means comprises
   means adjustable stepwise in opposite directions to select a predetermined value of said carrier signal amplitude to be supplied to said resonant circuit, and
   means responsive to adjustment of said last named means for generating stepping pulses and pulses indicating the direction of adjustment thereof.

6. Apparatus as in claim 1 in which said means for generating a first digital representation comprises converter means responsive to the amplitude of the carrier signal supplied to said series resonant circuit for producing a DC analog thereof, analog to digital converter means for converting said DC analog to a digital representation thereof, and in which said jointly responsive means comprises comparator means for comparing said first and second digital representations and controlling said attenuator means in response to the difference between said first and second representations.

* * * * *